US006921394B2

(12) United States Patent
Sayama et al.

(10) Patent No.: US 6,921,394 B2
(45) Date of Patent: Jul. 26, 2005

(54) DISPOSABLE ABSORBENT ARTICLE WITH EXCREMENT RECEIVING POCKET

(75) Inventors: Yasushi Sayama, Kagawa-ken (JP); Toshiyasu Yoshioka, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 101 days.

(21) Appl. No.: 10/320,218

(22) Filed: Dec. 16, 2002

(65) Prior Publication Data

US 2003/0114819 A1 Jun. 19, 2003

(30) Foreign Application Priority Data

Dec. 17, 2001 (JP) ........................................ 2001-383684

(51) Int. Cl.[7] .............................................. A61F 13/15
(52) U.S. Cl. .............................. 604/385.19; 604/385.28
(58) Field of Search ....................... 604/385.01, 385.09, 604/385.19, 385.28

(56) References Cited

U.S. PATENT DOCUMENTS

| 5,558,660 A | 9/1996 | Dreier |
| 5,897,544 A | 4/1999 | Rönnberg |
| 6,121,510 A | 9/2000 | Sauer |
| 6,371,950 B1 * | 4/2002 | Roslansky et al. ...... 604/385.19 |
| 6,638,260 B2 * | 10/2003 | Mishima ................. 604/385.01 |
| 6,824,534 B2 * | 11/2004 | Mishima et al. ....... 604/385.01 |
| 2002/0099351 A1 * | 7/2002 | Onishi et al. .......... 604/385.19 |
| 2002/0111594 A1 * | 8/2002 | Onishi et al. ................ 604/379 |
| 2002/0120248 A1 * | 8/2002 | Onishi et al. .......... 604/385.19 |

FOREIGN PATENT DOCUMENTS

| EP | 0 998 891 | 5/2000 | |
| JP | 8-196565 | 8/1996 | ........... A61F/13/15 |
| WO | WO 99/63921 | 12/1999 | |

* cited by examiner

*Primary Examiner*—Larry I. Schwartz
*Assistant Examiner*—Michael G Bogart
(74) *Attorney, Agent, or Firm*—Butzel Long (57) ABSTRACT

A disposable wearing article includes liquid-pervious topsheets, a liquid-impervious chassis and first and second liquid-absorbent panels. A first absorbent panel is covered with the topsheet and lies on the side of a front waist region. A second absorbent panel is interposed between the topsheet and chassis and continuously lies in a crotch region and a rear waist region. The first absorbent panel has a proximal end extending close to one of end flaps in a transverse direction and a first distal end supposed, along its transversely opposite side edges, to distal side edges of respective leakage-barrier cuffs so that an excrement receiving pocket adapted to open from the front waist region toward a crotch region is defined between the chassis and the first distal end of the first absorbent panel.

5 Claims, 10 Drawing Sheets

DISPOSABLE ABSORBENT ARTICLE WITH EXCREMENT RECEIVING POCKET

BACKGROUND OF THE INVENTION

This invention relates to a disposable wearing article for absorption and containment of bodily discharges.

Japanese Patent Application No. 1996-196565A discloses a disposable wearing article comprising a liquid-pervious topsheet facing wearer's body, a liquid-impervious backsheet facing away from the wearer's body and a liquid-absorbent core interposed between these sheets so as to define, in a longitudinal direction, a front waist region, a rear waist region and a crotch region extending between these waist regions wherein the core comprises an upper layer of core and a lower layer of core placed upon each other.

The upper layer of core consists of a front side core extending from the front waist region toward the crotch region and a rear side core extending from the rear waist region toward the crotch region. In this wearing article, inner ends of the front side core and the rear side core opposed to each other are spaced from each other by a given dimension in the longitudinal direction and the topsheet covering respective upper surfaces of the front and rear side core is folded down toward the lower layer of core along the inner ends of these front and rear side cores and then folded onto respective lower surfaces of the front and rear side cores.

In this wearing article, a first excrement receiving pocket is formed between the front side core and the lower layer of core so as to be opened from the front waist region toward the crotch region and a second excrement receiving pocket is formed between the rear side core and the lower layer of core so as to be opened from the rear waist region toward the crotch region. With such a wearing article, it is possible to receive and to retain excrement in these excrement receiving pockets and thereby to prevent feces from clinging to the wearer's skin.

In the wearing article disclosed in the above-cited Application, the upper layer of core and the lower layer of core are placed upon each other in the front and rear waist regions of the article, so a thickness of the core in the front and rear waist regions is larger than that of the core in the crotch region. With a consequence, a difference in level is inevitably formed between the upper layer of core and the lower layer of core in the crotch region and such a difference in level may give the wearer a feeling of incompatibility during use of the article.

Furthermore, this wearing article disclosed in the above-cited Application has no means biasing the respective inner ends of the front side core and the rear side core to be spaced upwardly from the lower layer of core. Consequently, the inner ends of the front and rear side cores may often remain in contact with the lower layer of core and make it difficult to open the respective excrement receiving pockets and make it even impossible to receive excrement in these excrement receiving pockets.

SUMMARY OF THE INVENTION

It is an object of this invention to provide a disposable wearing article improved to eliminate the anxiety that the wearer might experience a feeling of incompatibility with the article put on his or her body, on one hand, and to ensure that feces is reliably received and retained in the excrement receiving pockets, on the other hand.

According to this invention, there is provided a disposable wearing article having a front waist region, a rear waist region and a crotch region therebetween.

The disposable wearing article comprises a liquid-impervious chassis, a liquid-absorbent panel supported by the chassis, extending from the crotch region into the front and rear waist regions, a pair of leakage-barrier cuffs extending along transversely opposite side edges of the liquid-absorbent panel. Each of the leakage-barrier cuffs has a proximal side edge, a distal side edge and longitudinally opposite ends. The proximal side edge and the longitudinally opposite ends are fixed to the chassis and the distal side edge is provided therealong with an elastic member so that the leakage-barrier cuffs are biased to rise above the liquid-absorbent panel. The liquid-absorbent panel includes a first absorbent panel and a second absorbent panel. The first absorbent panel has a first proximal end, a first distal end and first transversely opposite side edges. The first proximal end is fixed to a vicinity of a longitudinal end of the chassis in the front waist region, the first transversely opposite side edges are located between the leakage-barrier cuffs, so that a first excrement receiving pocket is defined between the chassis and the first absorbent panel.

This invention includes the following embodiments. The first transversely opposite side edges of the first absorbent panel is supported by vicinities of the distal edges of the liquid-barrier cuffs, respectively.

The first absorbent panel comprises a first liquid-absorbent material and a first liquid-pervious topsheet covering at least an upper surface of the first liquid-absorbent material. The second absorbent panel comprises a second liquid-absorbent material and a second liquid-pervious topsheet covering an upper surface of the second liquid-absorbent material. A lower surface of the second absorbent material is joined to the chassis.

The second absorbent panel comprises a third absorbent panel and a fourth absorbent panel. The third absorbent panel has a second proximal end, a second distal end and second transversely opposite side edges. The second proximal end is fixed to a vicinity of a longitudinal end of the chassis in the rear waist region, the second transversely opposite side edges are supported by vicinities of the distal side edges of the leakage-barrier cuffs, respectively, so that a second excrement receiving pocket is defined between the chassis and the second absorbent panel. The third absorbent panel comprises a third liquid-absorbent material and a third liquid-pervious topsheet covering an upper surface of the third liquid-absorbent material. A lower surface of the third liquid-absorbent material is joined to the chassis. The fourth absorbent panel comprises a fourth liquid-absorbent material and a fourth liquid-pervious topsheet covering an upper surface of the fourth liquid-absorbent material. A lower surface of the fourth liquid-absorbent material is joined to the chassis.

DETAILED DESCRIPTION OF THE PREFERRED EMBODIMENTS

Details of the disposable wearing article according to this invention will be more fully understood from the description given hereunder and explaining an open-type diaper as an example in reference to the accompanying drawings.

Figure 1:
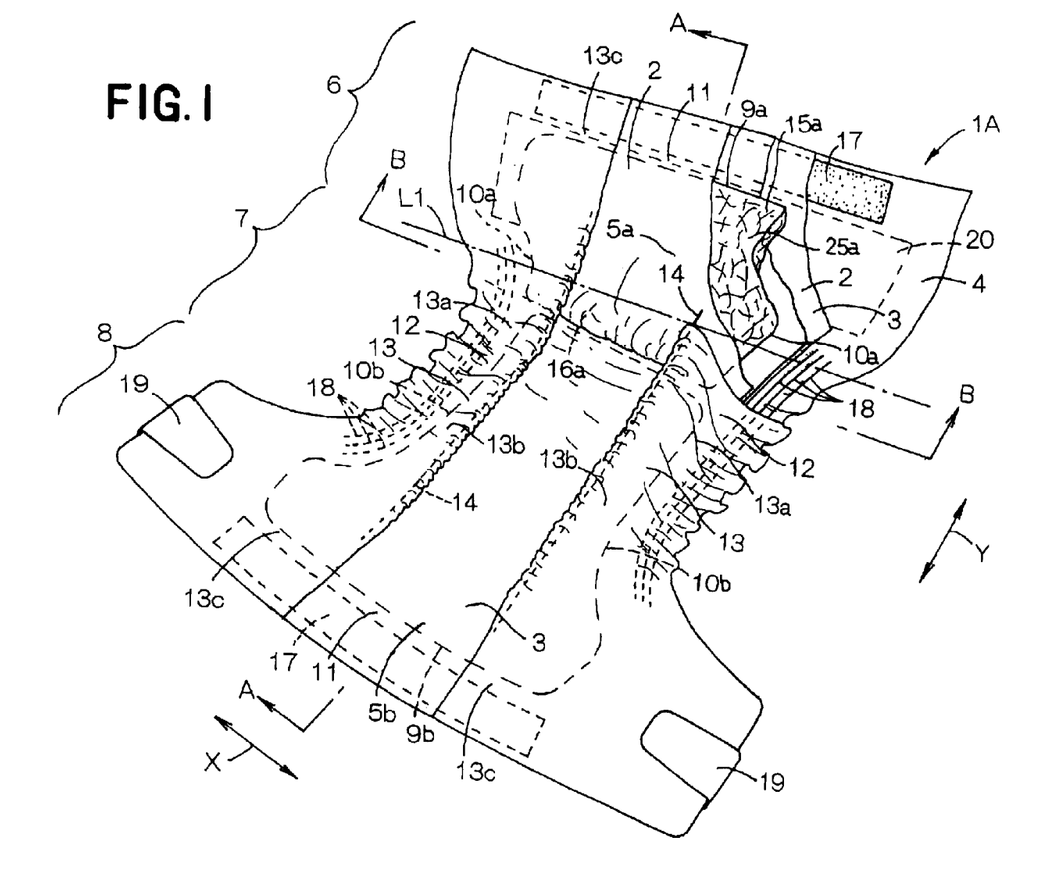
FIG. 1 is a partially cutaway perspective view showing a diaper.
Figure 2:
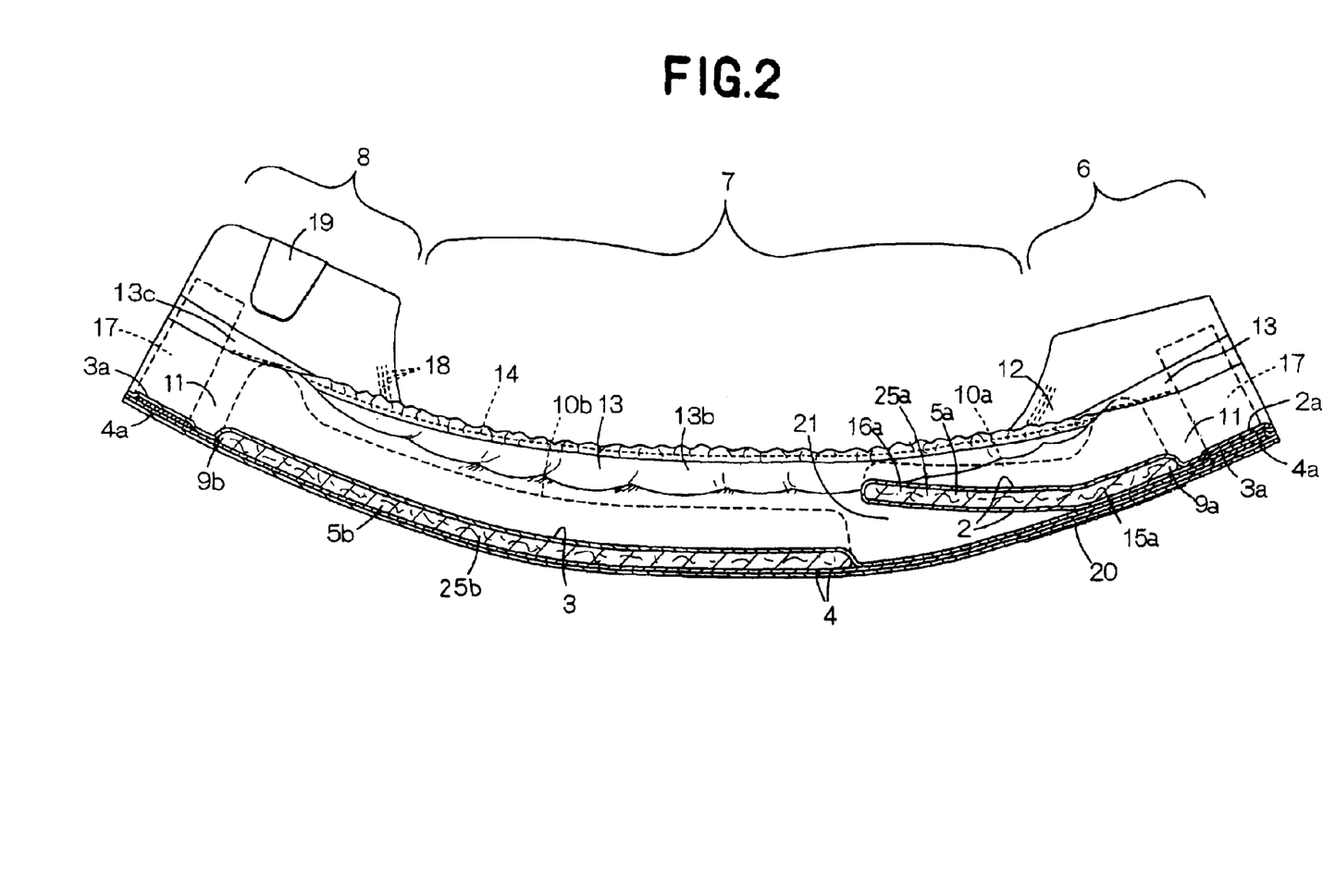
FIG. 2 is a cross-sectional view taken along a line A—A in FIG. 1.
Figure 3:
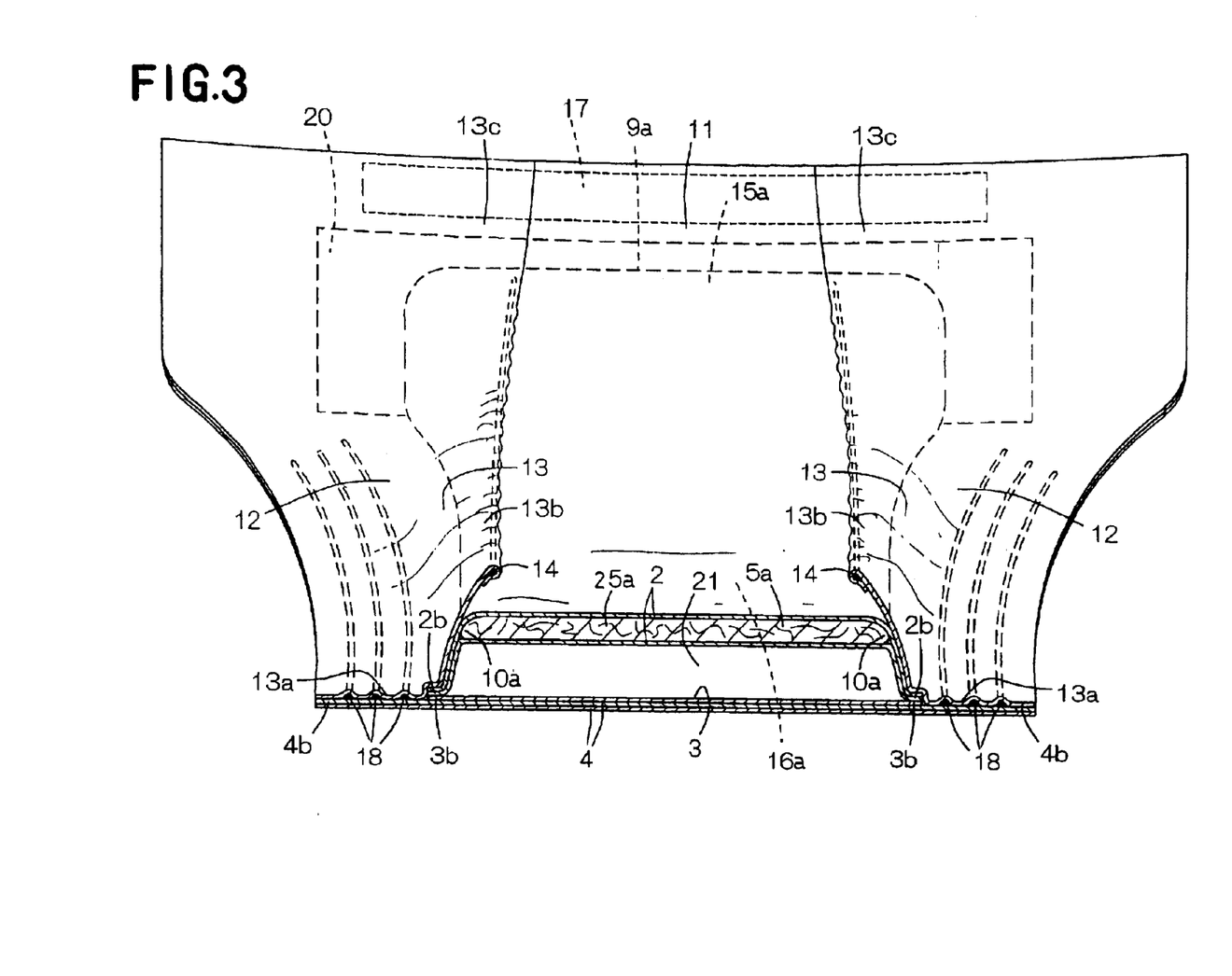
FIG. 3 is a cross-sectional view taken along a line B—B in FIG. 1.
Figure 4:
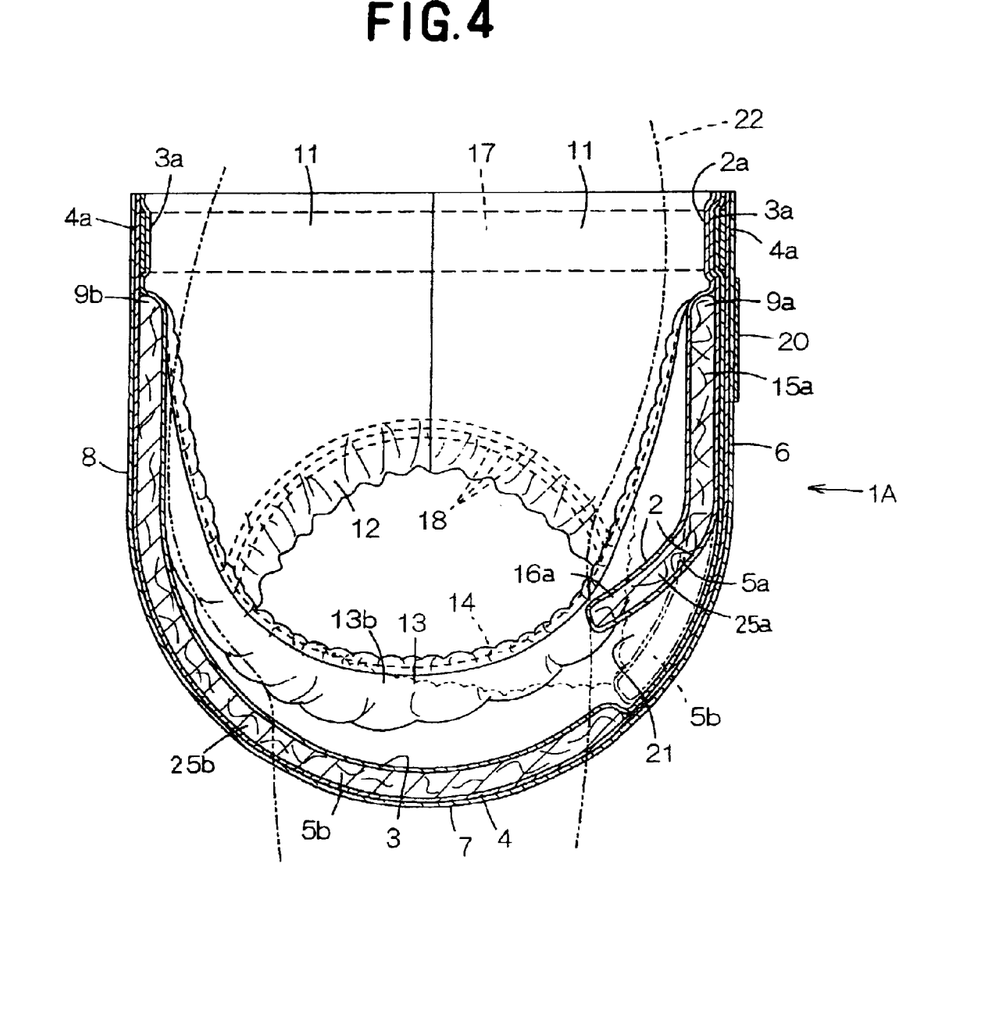
FIG. 4 is a perspective view showing the diaper of FIG. 1 as put on a wearer's body.

FIG. 1 is a partially cutaway perspective view showing the diaper 1A, FIG. 2 is a cross-sectional view taken along a line A—A in FIG. 1, FIG. 3 is a cross-sectional view taken along a line B—B in FIG. 1 and FIG. 4 is a perspective view showing the diaper 1A of FIG. 1 as put on a wearer's body. In FIG. 1, a transverse direction is indicated by an arrow X and a longitudinal direction is indicated by an arrow Y. In FIG. 4, a wearer 22 is indicated by a chain double-dashed line. Expression "upper surfaces of first and second absorbent panels 5a, 5b" should be understood to be the surfaces facing the wearer's body and expression "lower surfaces of these panels 5a, 5b" should be understood to be the surfaces facing away from the wearer's body.

The diaper 1A basically comprises a liquid-impervious chassis 4, first and second liquid-absorbent panels 5a, 5b supported by the chassis 4 and substantially liquid-impervious leakage-barrier cuffs 13.

The diaper 1A is composed, in the longitudinal direction, of a front waist region 6, a rear waist region 8 and a crotch region 7 extending between these waist regions 6, 8. End flaps 11 extend in the transverse direction immediately outside longitudinally opposite ends 9 of the panels 5a, 5b and side flaps 12 extend in the longitudinal direction immediately outside transversely opposite side edges 10 of the panels 5a, 5b. In the diaper 1A, the side flaps 12 in the crotch region 7 describe circular arcs which are convex inwardly in the transverse direction of the diaper 1A so that the diaper 1A has a hourglass-like shape as viewed in its plan view.

The chassis 4 comprises a hydrophobic fibrous nonwoven fabric and a breathable but liquid-impervious plastic film placed upon and joined to each other along surfaces thereof facing each other. The leakage-barrier cuffs 13 are made of a hydrophobic fibrous nonwoven fabric.

The leakage-barrier cuffs 13 lie on the respective side flaps 12 and extend in the crotch region 7 and further extend into the front and rear waist regions 6, 8 in the longitudinal direction. Each of the cuffs 13 has a proximal side edge 13a fixed to the associated side flap 12 and extending in the longitudinal direction, a distal side edge 13b biased to rise above the liquid-absorbent panels 5a, 5b and extending in the longitudinal direction and longitudinally opposite ends 13c collapsed inwardly in the transverse direction of the diaper 1A and fixed to the end flaps 11 in such a collapsed state. An elastically stretchable member 14 extending in the longitudinal direction is secured to the distal side edge 13b in a stretched state. The elastic member 14 is covered with a part of the distal side edge 13b.

The liquid-absorbent panels 5a, 5b are supported by the chassis 4 so as to extend in the crotch region 7 further into the front and rear waist regions 6, 8. The panels 5a, 5b are separated in the longitudinal direction in the vicinity of a transverse boundary line L1 defined between the front waist region 6 and the crotch region 7. A first absorbent panel 5a lies on the side of the front waist region 6 and a second absorbent panel 5b lies on the crotch region 7 as well as on the rear waist region 8.

The first absorbent panel 5a includes a first absorbent material 25a and a liquid-pervious topsheet 2 (a first liquid-pervious topsheet) entirely covering the first absorbent material 25a. The first absorbent panel 5a has, a first proximal end 15a, a first distal end 16a and first transversely opposite side edges 10a. The first proximal end 15a is fixed to the chassis 4 through the intermediately of a liquid-pervious topsheet 3. The first distal end 16a is not fixed to the chassis 4 but spaced upwardly from the chassis 4. The first transversely opposite side edges 10a is supported by the vicinities of the distal side edges 13b of the respective leakage-barrier cuffs 13.

The second absorbent panel 5b comprises a second liquid absorbent material 25b and the liquid-pervious topsheet 3 (a second liquid-pervious topsheet) covering an upper surface of the second absorbent material 25b. A lower surface of the panel 5b is fixed to the chassis 4. The topsheet 3 is placed upon and joined to the chassis 4 along surfaces thereof outside the second liquid absorbent material 25b. The topsheet 2 entirely covering the first absorbent panel 5a is joined to the chassis 4 through the intermediary of the topsheet 3 at the first proximal end 15a. The topsheets 2, 3 are made of a hydrophilic fibrous nonwoven fabric.

Band-like waist-surrounding elastic members 17 extending in the transverse direction are attached in a stretched state to the respective end flaps 11. Each of the side flaps 12, on the other hand, is provided with a plurality of tigh-surrounding elastic members 18 extending in the longitudinal direction attached thereto in a stretched state. The side flaps 12 in the rear waist region 8 are provided with tape fasteners 19 extending inwardly in the transverse direction. In the front waist region 6, the chassis 4 is provided on its outer surface with a rectangular target tape 20 serving as a landing zone for the tape fasteners 19. Each of these tape fasteners 19 has its free end zone coated with an adhesive (not shown) and temporarily fixed to the associated side flap. The tape fasteners 19 as well as the target tape 20 are made of a flexible plastic film.

To wear the diaper 1A, the side flaps 12 in the rear waist region 8 are placed upon the outer surfaces of the side flaps 12 in the front waist region 6, then the distal end of the respective tape fasteners 19 are fixed on the target tape 20 by means of the adhesive and thereby the front waist region 6 and the rear waist region 8 are connected to each other. With the front and rear waist regions 6, 8 connected to each other in this manner, the diaper 1A is formed with a waist-hole and a pair of leg-holes.

When the diaper 1A is left to curve in the longitudinal direction with the panels 5a, 5b inside, the elastic members 14 contract and thereby distal side edges 13b of the respective leakage-barrier cuffs 13 rise on the liquid-absorbent panels 5a, 5b. In the diaper 1A, the distal side edges 13b of the rising cuffs 13 form barriers against bodily discharges and prevent the bodily discharges from leaking between the crotch region 7 and the wearer's thighs.

In the diaper 1A, an excrement receiving pocket 21 (first excrement receiving pocket) adapted to open from the front waist region 6 toward the crotch region 7 is formed between the chassis 4 and the first distal end 16a of the first absorbent panel 5a. The distal side edges 13b of the rising cuffs 13 lift the first distal end 16a of the first absorbent panel 5a above the chassis 4 and thereby prevent the first distal end 16a of the first absorbent panel 5a from coming in contact with the chassis 4. Consequently, there is no possibility that the excrement receiving pocket 21 might be collapsed. Of bodily discharges, feces can be reliably received in the excrement receiving pocket 21 and the first absorbent panel 5a prevents feces from coming in contact with a crotch region of the wearer 22. In this way, it is unlikely that feces might cling to the crotch region of the wearer 22.

In the diaper 1A, the first distal end 16a of the first absorbent panel 5a is spaced upwardly from the chassis 4 so that a difference in level is defined between the first distal end 16a of the first absorbent panel 5a and the second absorbent panel 5b. However, when a pressure due to the wearer's body weight is exerted on the first absorbent panel 5a, the first distal end 16a of the first absorbent panel 5a comes in contact with the chassis 4 without overlapping the second absorbent panel 5b as indicated by a chain double-dashed line in FIG. 4 and no difference in level is defined between these panels 5a, 5b. In the front and rear waist regions 6, 8 of the diaper 1A, it is unlikely that the liquid-absorbent panel 5 might become bulky and the difference in level between the first absorbent panel 5a and the second absorbent panel 5b is eliminated under a pressure due to the body weight of the wearer 22. In this way, there is no anxiety that the wearer 22 might experience the feeling of incompatibility during use of the diaper 1A.

In the end flaps 11 lying the front waist region 6, longitudinal ends 2a, 3a of the respective topsheets 2, 3 and the longitudinal end 4a of the chassis 4 extend outwardly beyond the outer end 9a of the first absorbent panel 5a in the longitudinal direction. The ends 2a, 3a, 4a of the these sheets 2, 3, 4 are placed upon and joined one to another. In the end flaps 11 lying in the rear waist region 8, on the other hand, the longitudinal end 3a of the topsheet 3 and the longitudinal end 4a of the chassis 4 extend outwardly beyond the outer end 9b of the second absorbent panel 5b in the longitudinal direction. The ends 3a, 4a of these sheets 3, 4 are placed upon and joined together. The waist-surrounding elastic members 17 are interposed between the longitudinally opposite ends 3a of the topsheet 3 and the longitudinally opposite ends 4a of the chassis 4 and secured to these ends 3a, 4a.

In the side flaps 12, transversely opposite side edges 2b of the topsheet 2 and transversely opposite side edges 3b of the topsheet 3 extend outwardly slightly beyond the transversely opposite side edges 10a, 10b of the first and second absorbent panels 5a, 5b in the transverse direction. Transversely opposite side edges 4b of the chassis 4 and the proximal side edges 13a of the respective leakage-barrier cuffs 13 further extend outwardly beyond the side edges 2b, 3b of the respective topsheets 2, 3. In the side flaps 12, the side edges 2b, 3b, 4b, 13a of these sheets 2, 3, 4, 13 are placed upon and joined one to another. The thigh-surrounding elastic members 18 are interposed between the side edges 4b of the chassis 4 and the proximal side edges 13a of the leakage-barrier cuffs 13 and secured to these side edges 4b, 13a of the respective sheets 4, 13.

Figure 5:
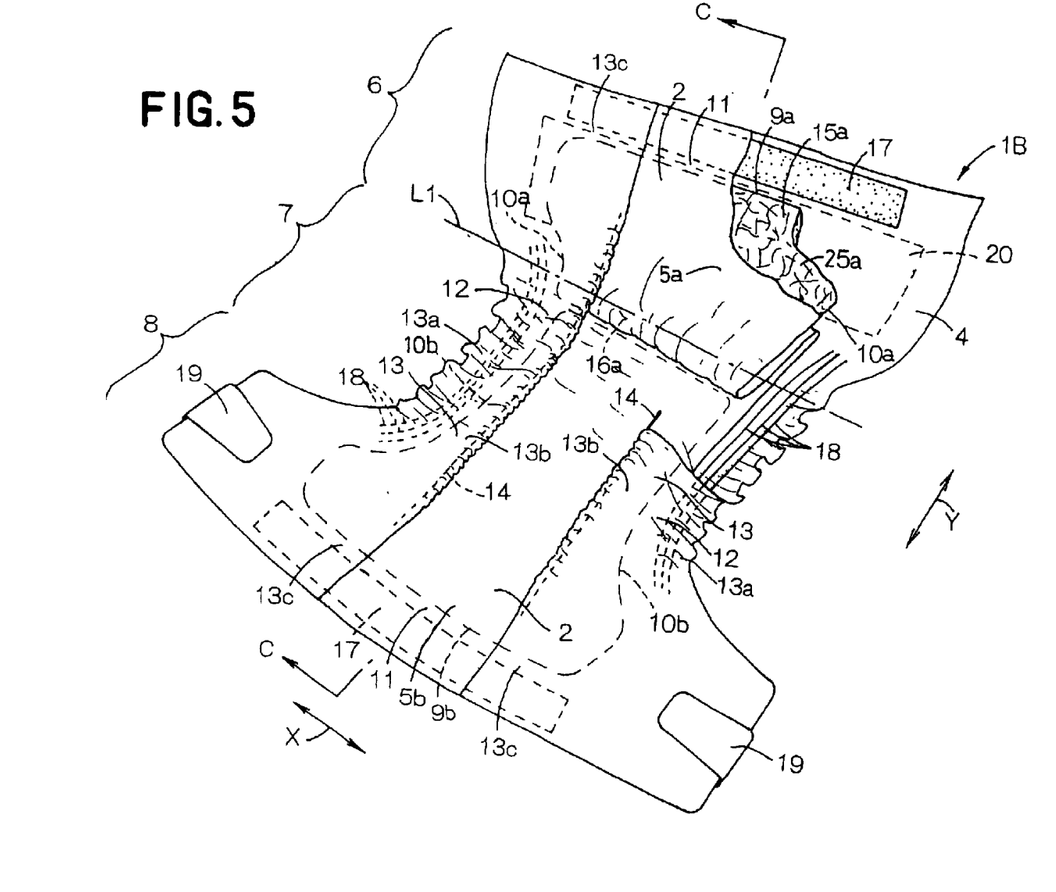
FIG. 5 is a partially cutaway perspective view showing one embodiment of the diaper according to this invention.
Figure 6:
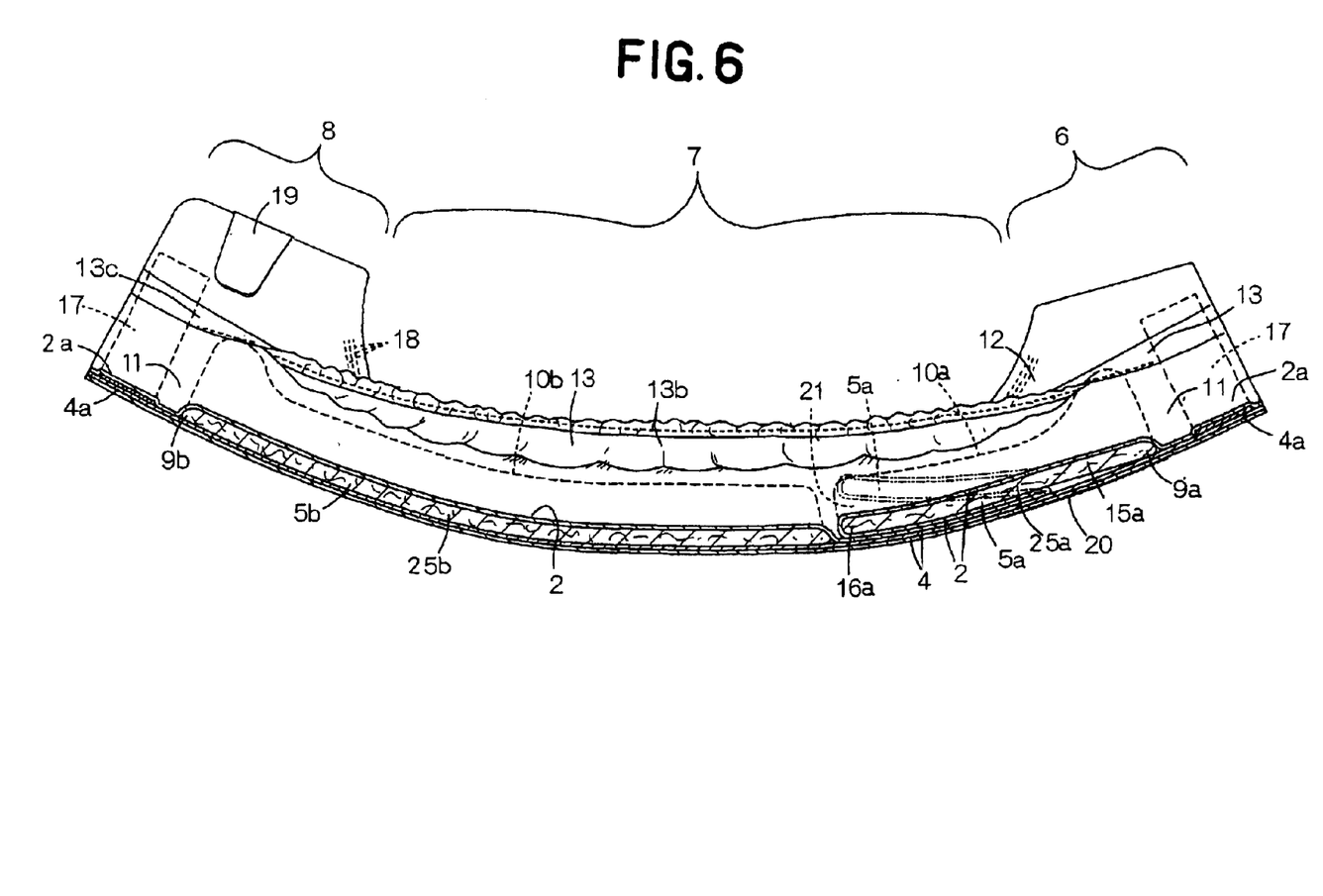
FIG. 6 is a cross-sectional view taken along a line C—C in FIG. 5.

FIG. 5 is a partially cutaway perspective view showing one preferred embodiment 1B of the diaper according to this invention and FIG. 6 is a cross-sectional view taken along a line C—C in FIG. 5. In FIG. 5 also, the transverse direction is indicated by the arrow X and the longitudinal direction is indicated by the arrow Y. Similarly to the diaper 1A of FIG. 1, this diaper 1B also comprises the liquid-impervious chassis 4, the first absorbent panel 5a extending in the front waist region 6, the second absorbent panel 5b extending in the crotch region 7 as well as the rear waist region 8 and the substantially liquid-impervious leakage-barrier cuffs 13 extending in the longitudinal direction on the respective side flaps 12. This diaper 1B differs from the diaper 1A in a specific arrangement as will be described.

In the case of the diaper 1B, the first and second absorbent panels 5a, 5b are covered with the contiguous topsheet 2. The topsheet 2 is folded back from the first distal end 16a of the first absorbent panel 5a onto the lower surface of the absorbent panel 5a and then folded back from the first proximal end 15a of the panel 5a toward the second absorbent panel 5b so as to extend to the end flap 11 in the rear waist region 8. As shown in FIG. 6, the topsheet 2 is tucked under the lower surface of the first absorbent panel 5a so as to present a Z-shaped cross-section. In the first absorbent panel 5a, the first distal end 16a is not fixed to the chassis 4 and the first transversely opposite side edges 10a are not fixed to the distal side edges 13b of the respective leakage-barrier cuffs 13.

In the case of this diaper 1B, the mass of feces discharged onto the crotch region 7 causes the second absorbent panel 5b to be spaced from the crotch region of the wearer 22 and, as a result, the first distal end 16a of the first absorbent panel 5a is spaced upwardly from the chassis 4 as indicated by imaginary lines in FIG. 6. In this way, the excrement receiving pocket 21 (first excrement receiving pocket) adapted to open from the front waist region 6 toward the crotch region 7 is defined between the first distal end 16a spaced upwardly from the chassis 4 in this manner. The diaper 1B also can reliably receive the discharged feces in the excrement receiving pocket 21 and thereby can advantageously prevent any amount of the discharged feces from clinging to the crotch region of the wearer 22. In the diaper 1B prior to discharge of feces, no difference in level is formed between the first absorbent panel 5a and the second absorbent panel 5b. With an advantageous consequence, these panels 5a, 5b are not bulky in the front waist region 6 and the rear waist region 8, respectively, and the wearer 22 is free from the feeling of incompatibility.

Figure 7:
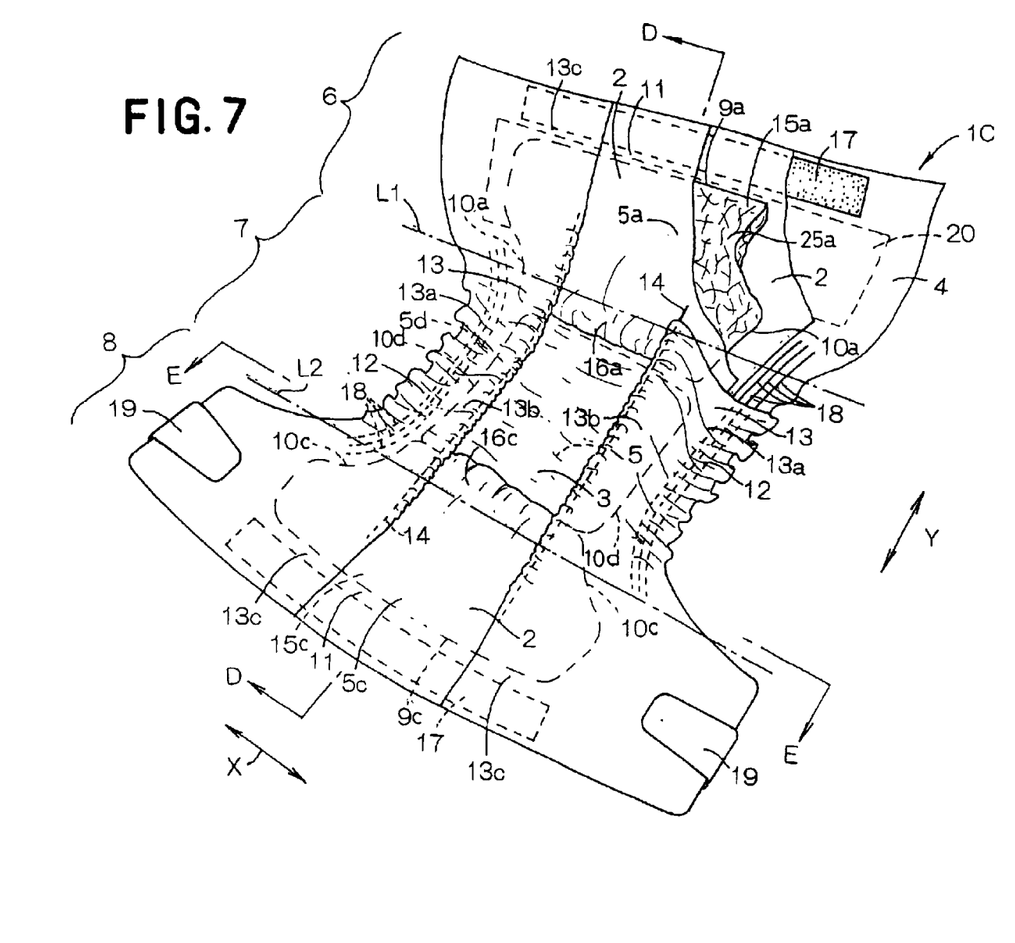
FIG. 7 is a partially cutaway perspective view showing another embodiment of the diaper according to this invention.
Figure 8:
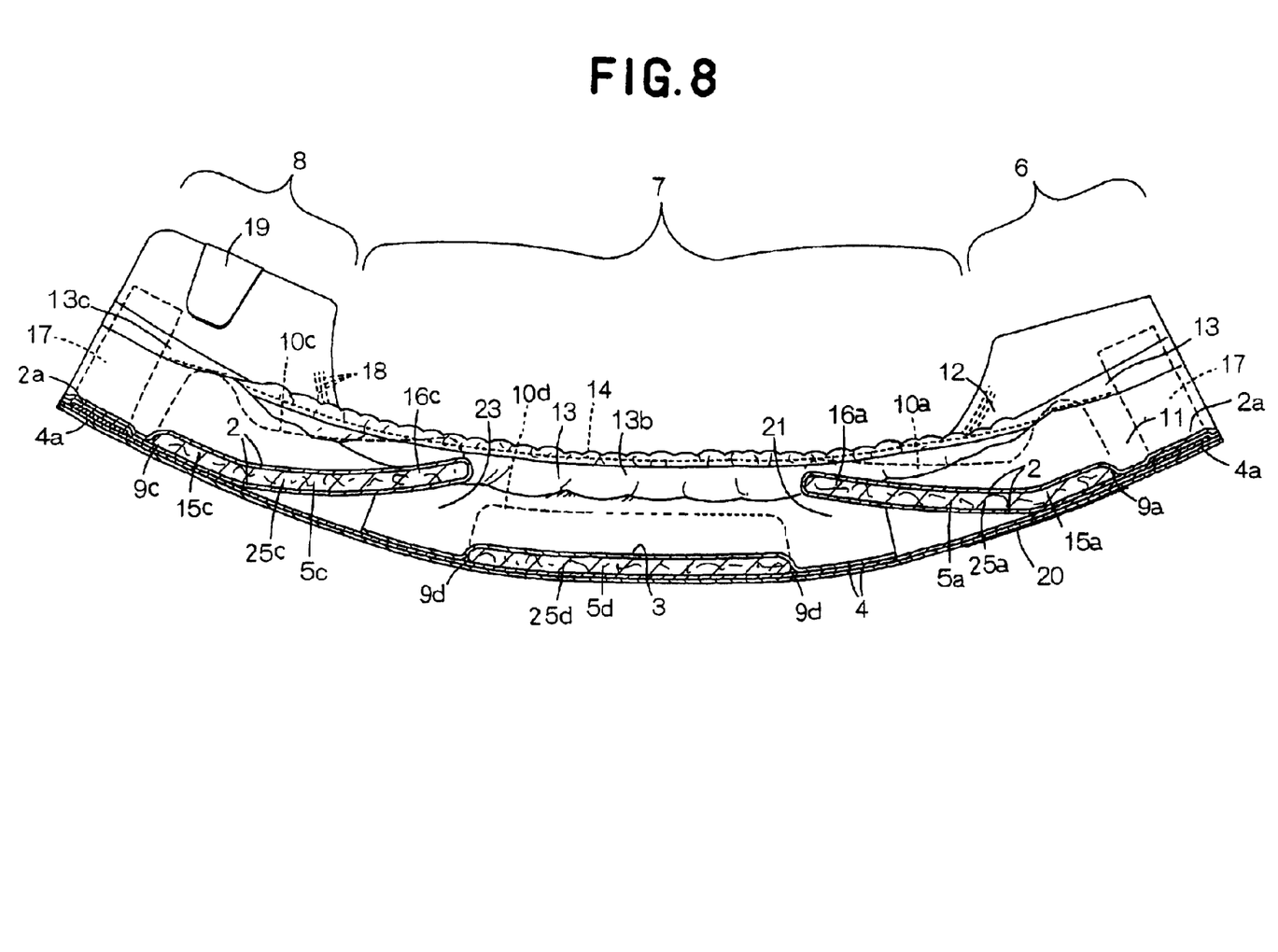
FIG. 8 is a cross-sectional view taken along a line D—D in FIG. 7.
Figure 9:
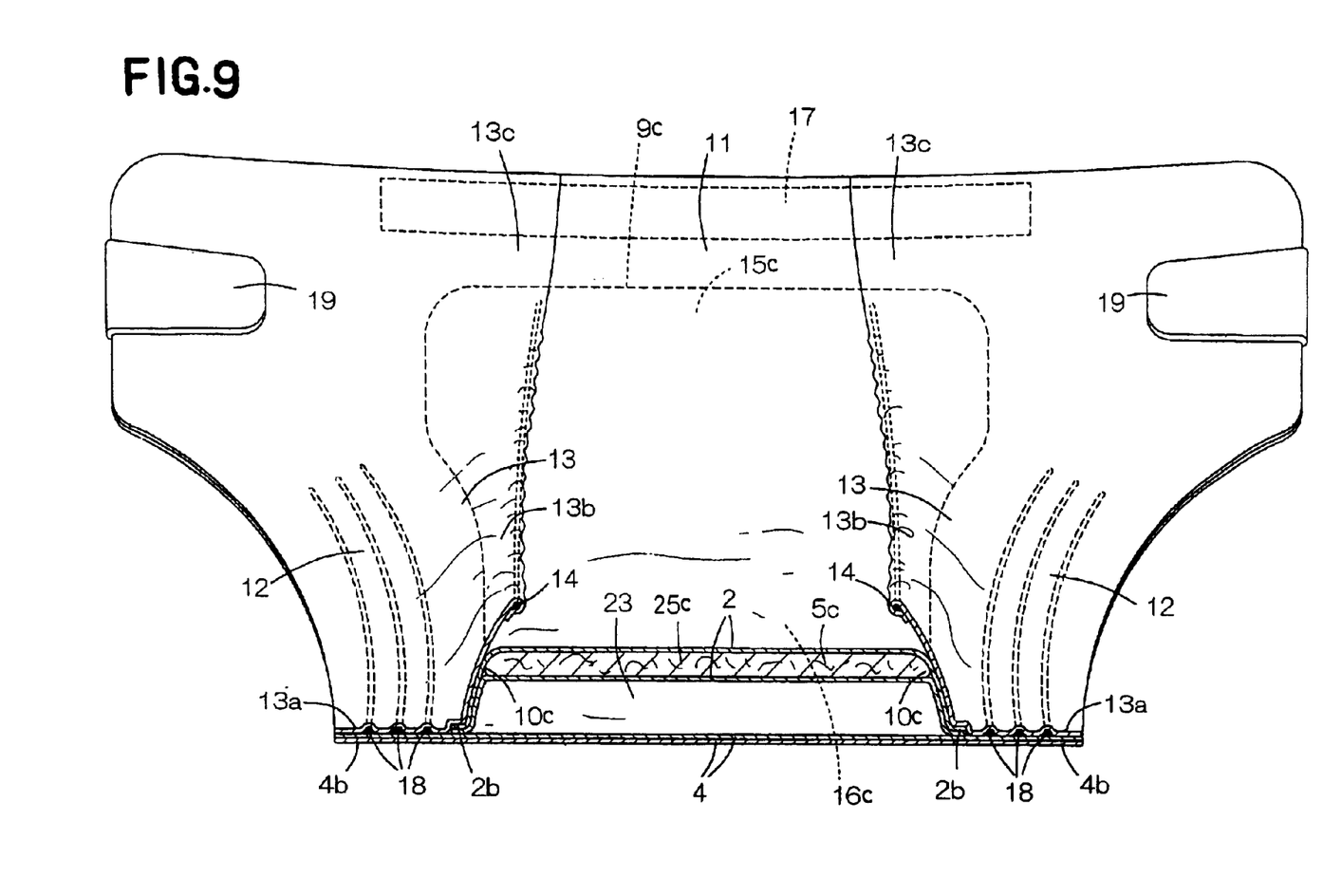
FIG. 9 is a cross-sectional view taken along a line E—E in FIG. 7.
Figure 10:
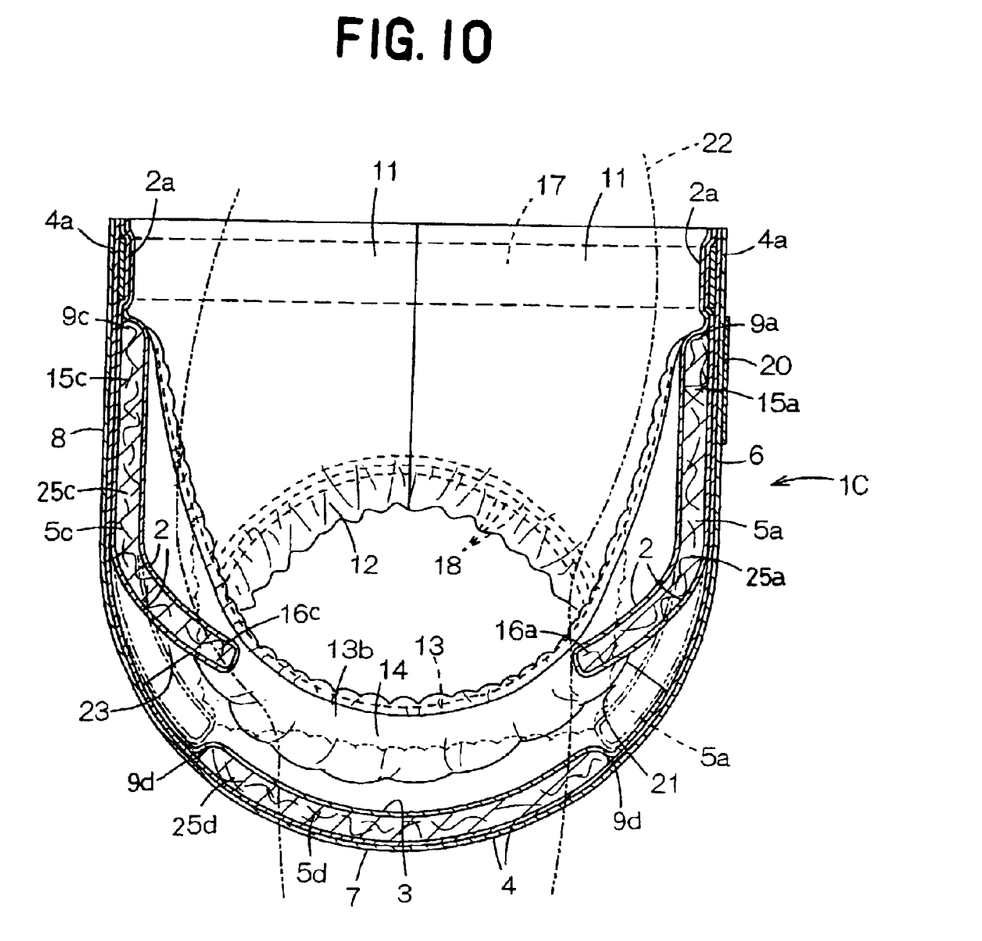
FIG. 10 is a perspective view showing the diaper of FIG. 7 as put on a wearer's body.

FIG. 7 is a partially cutaway perspective view showing another preferred embodiment 1C of the diaper according to this invention, FIG. 8 is a cross-sectional view taken along a line D—D in FIG. 7, FIG. 9 is a cross-sectional view taken along a line E—E in FIG. 7 and FIG. 10 is a perspective view showing the diaper 1C of FIG. 7 as put on a wearer's body. In FIG. 7 also, the transverse direction is indicated by the arrow X and the longitudinal direction is indicated by the arrow Y. In FIG. 10, the wearer 22 is indicated by a chain double-dashed line.

Similarly to the diaper 1A of FIG. 1, the diaper 1C comprises the liquid-impervious chassis 4, first, third and fourth liquid-absorbent panels 5a, 5c, 5d and the substantially liquid-impervious leakage-barrier cuffs 13. This diaper 1C differs from the diaper 1A of FIG. 1 in a specific arrangement as will be described.

The first, third and fourth absorbent panels 5a, 5c, 5d are separated in the longitudinal direction in the vicinity of a boundary line L1 defined between the front waist region 6 and the crotch region 7 and in the vicinity of a boundary line L2 defined between the rear waist region 8 and the crotch region 7. A first absorbent panel 5a lies on the side of the front waist region 6, a third absorbent panel 5c lies on the side of the rear waist region 8 and a fourth absorbent panel 5d lies on the crotch region 7. To prepare the first, third and fourth absorbent panels 5a, 5c, 5d, the second absorbent panel 5b of FIG. 1 may be divided into two in the vicinity of the boundary line L2.

The third absorbent panel 5c includes a third absorbent material 25c and a liquid-pervious topsheet 2 (a third liquid-pervious topsheet) entirely covering the third absorbent material 25c. Both the first absorbent panel 5a and the third absorbent panel 5c have surfaces thereof inclusive of upper and lower surfaces entirely covered with the topsheet 2. The third absorbent panel 5c has a second proximal end 15c extending close to the associated end flap 11 in the transverse direction, a second distal end 16c and second transversely opposite side edges 10c. The proximal ends 15a, 15c of these absorbent panels 5a, 5c are fixed to the chassis 4 through the intermediary of the topsheet 3. The distal ends 16a, 16c of these panels 5a, 5c are not fixed to the chassis 4 but spaced upwardly from the chassis 4. The distal ends 16a, 16c of these panels 5a, 5c are supported by the vicinities of the distal side edges 13b of the respective leakage-barrier cuffs.

The fourth absorbent panel 5d comprises a fourth liquid absorbent material 25d and the liquid-pervious topsheet 3 (a fourth liquid-pervious topsheet) covering an upper surface of the fourth absorbent material 25d. The fourth absorbent panel 5d has its upper surface covered with the topsheet 3 and its lower surface covered with the chassis 4 and is fixed to at least one of these sheets 3, 4. The topsheet 3 covering the fourth absorbent panel 5d extends outwardly in the longitudinal direction slightly beyond the longitudinally opposite ends 9d of the fourth absorbent panel 5d and reaches neither the end flaps 11 nor the outer ends 9a, 9c of the first and third absorbent panels 5a, 5c. In the side flaps 12, transversely opposite side edges 2b, 3b of the topsheets 2, 3 extend outwardly slightly beyond the transversely opposite side edges 10a, 10c, 10d of the first, third and fourth absorbent panels 5a, 5c, 5d in the transverse direction.

In the diaper 1C, a first excrement receiving pocket 21 adapted to open from the front waist region 6 toward the crotch region 7 is defined between the chassis 4 and the first distal end 16a of the first absorbent panel 5a and a second excrement receiving pocket 23 adapted to open from the rear waist region 8 toward the crotch region 7 is defined between the chassis 4 and the second distal end 16c of the third absorbent panel 5c. Feces discharged onto this diaper 1C is reliably received in these excrement receiving pockets 21, 23 and these panels 5a, 5c well prevent the feces from coming in contact with the crotch region of the wearer 22. Consequently, there is no possibility that any amount of the discharged feces from clinging to the crotch region of the wearer 22. With this diaper 1C, even if the feces discharged thereon moves toward the rear waist region 8, such feces will be received in the second excrement receiving pocket 23, so it is possible for this diaper 1C to prevent any amount of the discharged feces from clinging to the crotch region of the wearer not only in the front waist region 6 but also in the rear waist region 8.

In the diaper 1C also, the distal side edges 13b of the rising cuffs 13 lift the first and second distal ends 16a, 16c of the first and third absorbent panels 5a, 5c above the chassis 4. In this way, it is unlikely that the distal ends 16a, 16c of the panels 5a, 5c might come in contact with the chassis 4 and the excrement receiving pockets 21, 23 might be collapsed.

In the diaper 1C, there is a difference in level between the distal ends 16a, 16c of the panels 5a, 5c and the fourth absorbent panel 5d. However, the distal ends 16a, 16c of the first and third absorbent panels 5a, 5c come in contact with the chassis 4 without overlapping each other as indicated by imaginary lines in FIG. 10 when a pressure due to the body weight is placed on these panels 5a, 5c. Thus differences in level possibly defined by these panels 5a, 5c, 5d are eliminated. In the diaper 1C, the panels 5a, 5c are not bulky in the front and rear waist regions 6, 8 and the pressure due to the body weight of the wearer 22 eliminates any difference in level defined by these panels 5a, 5c, 5d. In this way, it is unlikely that the diaper 1C might give the wearer 22 the feeling of incompatibility.

The topsheets 2, 3 may be formed using a material selected from a group including a hydrophilic fibrous nonwoven fabric, a hydrophobic fibrous nonwoven fabric having a plurality of pores and a liquid-pervious plastic film having a plurality of fine pores. The chassis 4 may be formed using a material selected from a group including a hydrophobic fibrous nonwoven fabric, a breathable but liquid-impervious plastic film, a composite nonwoven fabric consisting of two or more layers of a hydrophobic fibrous nonwoven fabric laminated one with another and a composite sheet consisting of a hydrophobic nonwoven fabric and a breathable but liquid-impervious plastic film.

It is also possible to form the chassis 4 and the leakage-barrier cuffs 13 using a composite nonwoven fabric comprising a melt blown fibrous nonwoven fabric having a high water-resistance and two layers of a spun bond fibrous nonwoven fabric having a high strength and a flexibility sandwiching the melt blown fibrous nonwoven fabric therebetween.

The nonwoven fabric may be selected from a group including products obtained by spun lacing, needle punching, melt blowing, thermal bonding, spun bonding, chemical bonding and air-through processes. Component fibers of the nonwoven fabric may be selected from a group including polyolefine-, polyester- and polyamide-based fibers and core-sheath-type and side-by-side-type conjugated fibers of polyethylene/polypropylene and polyethylene/polyester.

The absorbent panels 5a, 5b, 5c, 5d comprise a mixture of fluff pulp and super-absorbent polymer particles or a mixture of fluff pulp, super-absorbent polymer particles and thermoplastic synthetic resin fibers compressed to a desired thickness. Preferably, the absorbent panels 5a, 5b, 5c, 5d are entirely covered with a tissue paper to prevent possibility that the panels 5a, 5b, 5c, 5d might get out of shape or the polymer particles might fall off from the panels 5a, 5b, 5c, 5d. The polymer particles may be selected from a group including of a starch-based polymer, a cellulose-based polymer or a synthetic polymer.

Joining of the topsheets 2, 3 and the chassis 4, joining of the leakage-barrier cuffs 13, joining of the absorbent panels 5a, 5b, 5c, 5d, and securing of the elastic members 14, 17, 18 may be carried out using hot melt adhesives or welding techniques such as a heat-sealing and a sonic-sealing.

This invention is applicable, not only to an open-type disposable diaper having the front and rear waist regions adapted to be connected as the diaper is being put on the wearer's body but also to a pants-type disposable diaper having front and rear waist regions previously connected together so as to define a waist-hole and a pair of leg-holes.

The disposable wearing article according to this invention has the advantageous effects that a mass of feces discharged onto the crotch region causes the second absorbent panel to be spaced downwardly from the crotch region of the wearer and causes the first distal end of the first absorbent panel to be spaced upwardly from the chassis so as to define, between the chassis and the first distal end of the first absorbent panel, the first excrement receiving pocket adapted to open from the front waist region toward the crotch region. It is possible for this wearing article to receive the feces discharged thereon in this first excrement receiving pocket and thereby to prevent any amount of the feces from clinging to the crotch region of the wearer. In the wearing article prior to discharge of feces, no difference in level is defined between the first absorbent panel and the second absorbent panel and therefore the article put on the wearer's body gives the wearer no feeling of incompatibility. Furthermore, this wearing article enables the feces received in the first excrement receiving pocket to be visually recognized from the exterior and facilitates a timing for exchange of the article to be known.

With the article in which the first transversely opposite side edges of the first absorbent panel are supported by the distal side edges of the respective cuffs, the distal side edges of the rising cuffs lift the first distal end of the first absorbent panel above the chassis. That is, there is no possibility that the distal end of the first absorbent panel might come in contact with the chassis and the first excrement receiving pocket might be collapsed. In this way, feces discharged on the article can be reliably received in the first excrement receiving pocket. In this wearing article, the liquid-absorbent panel is not bulky in the front and rear waist regions and, when a pressure due to the wearer's body weight is placed on the first absorbent panel, the difference in level defined between the first distal end of the first absorbent panel and the second absorbent panel is eliminated. Consequently, the wearer of the article is free from any feeling of incompatibility.

With the article having the first, third and fourth absorbent panels, in addition of the first excrement receiving pocket, the second excrement receiving pocket adapted to open from the rear waist region toward the crotch region is defined between the chassis and the second distal end of the third absorbent panel. It is possible for the article according to this embodiment to receive the feces discharged on the article not only in the first excrement receiving pocket but also in the second excrement receiving pocket. In this way, there is no anxiety that any amount of the feces might cling to the front waist region as well as the rear waist region.

With the article having the first, third and fourth absorbent panels and the first and second distal ends of the first and third absorbent panels are supported by the distal side edges of the respective leakage-barrier cuffs, the distal side edges of the rising cuffs lift the first and second distal ends of the first and third absorbent panels above the chassis. Therefore, there is no possibility that first and second distal ends of the first and third absorbent panels might come in contact with the chassis and the first and second excrement receiving pockets might be collapsed. In this way, feces discharged on the article can be reliably received in the first and second excrement receiving pockets. In this wearing article, the liquid-absorbent panels are not bulky in the front and rear waist regions and, when a pressure due to the wearer's body weight is placed on the first and third absorbent panels, the differences in level defined between the first and second distal ends of the first and third absorbent panels and the fourth absorbent panel are eliminated. Consequently, the wearer of the article is free from any feeling of incompatibility.

What is claimed is:

1. A disposable wearing article having a front waist region, a rear waist region and a crotch region therebetween, said disposable wearing article comprising:
    a liquid-impervious chassis;
    a liquid-absorbent panel supported by said chassis, said liquid-absorbent panel extending from said crotch region into said front and rear waist regions;
    a pair of leakage-barrier cuffs extending along transversely opposite side edges of said liquid-absorbent panel, each of said leakage-barrier cuffs having a proximal side edge, a distal side edge and longitudinally opposite ends, with said proximal side edge and said longitudinally opposite ends fixed to said chassis and with said distal side edge provided therealong with an elastic member so that said leakage-barrier cuffs are biased to rise above said liquid-absorbent panel;
    said liquid-absorbent panel including a first absorbent panel and a second absorbent panel; and
    said first absorbent panel having a first proximal end, a first distal end and first transversely opposite side edges, said first proximal end being fixed to a vicinity of a longitudinal end of said chassis in said front waist region, said first transversely opposite side edges being located between said leakage-barrier cuffs, so that a first excrement receiving pocket is defined between said chassis and said first absorbent panel.

2. The disposable wearing article according to claim 1, wherein said first transversely opposite side edges of said first absorbent panel are supported by said liquid-barrier cuffs near vicinities of said distal edges of said liquid-barrier cuffs, respectively.

3. The disposable wearing article according to claim 1, wherein said first absorbent panel comprises a first liquid-absorbent material and a first liquid-pervious topsheet covering at least an upper surface of said first absorbent material.

4. The disposable wearing article according to claim 1, wherein said second absorbent panel comprises a second liquid-absorbent material and a second liquid-pervious topsheet covering an upper surface of said second absorbent material, a lower surface of said second absorbent material being joined to said chassis.

5. The disposable wearing article according to claim 1, wherein said second absorbent panel comprises a third absorbent panel and a fourth absorbent panel, said third absorbent panel having a second proximal end, a second distal end and second transversely opposite side edges, said second proximal end being fixed to said chassis in a vicinity of a longitudinal end of said chassis in said rear waist region, said second transversely opposite side edges being supported by said leakage-barrier cuffs in vicinities of said distal side edges of said leakage-barrier cuffs, respectively, so that a second excrement receiving pocket is defined between said chassis and said second absorbent panel, said third absorbent panel comprises a third liquid-absorbent material and a third liquid-pervious topsheet covering an upper surface of said third liquid-absorbent material, a lower surface of said third absorbent material being joined to said chassis, said fourth absorbent panel comprises a fourth liquid-absorbent material and a fourth liquid-pervious topsheet covering an upper surface of said fourth liquid-absorbent material, a lower surface of said fourth liquid-absorbent material being joined to said chassis.

* * * * *